US006974527B2

(12) United States Patent
Liu et al.

(10) Patent No.: US 6,974,527 B2
(45) Date of Patent: Dec. 13, 2005

(54) MULTIDIMENSIONAL SEPARATIONS EMPLOYING AN ARRAY OF ELECTROPHORESIS CHANNELS

(75) Inventors: ChangSheng Liu, State College, PA (US); Kevin Le Van, State College, PA (US)

(73) Assignee: SpectruMedix LLC, State College, PA (US)

( * ) Notice: Subject to any disclaimer, the term of this patent is extended or adjusted under 35 U.S.C. 154(b) by 406 days.

(21) Appl. No.: 09/874,331

(22) Filed: Jun. 6, 2001

(65) Prior Publication Data

US 2002/0033336 A1 Mar. 21, 2002

Related U.S. Application Data

(60) Provisional application No. 60/209,588, filed on Jun. 6, 2000.

(51) Int. Cl.[7] .................... G01N 27/447; G01N 27/453; G01N 30/02
(52) U.S. Cl. .......................... 204/452; 204/603; 422/70
(58) Field of Search .................... 204/451, 452, 204/601, 603; 422/70; 210/656; 702/19, 22

(56) References Cited

U.S. PATENT DOCUMENTS

| 5,139,630 | A | * | 8/1992 | Chen | 204/451 |
| 5,228,960 | A | * | 7/1993 | Liu et al. | 204/451 |
| 5,916,428 | A | * | 6/1999 | Kane et al. | 204/601 |
| 6,387,234 | B1 | * | 5/2002 | Yeung et al. | 204/451 |
| 6,537,432 | B1 | * | 3/2003 | Schneider et al. | 204/450 |

FOREIGN PATENT DOCUMENTS

| JP | 64-80852 A | * | 3/1989 | G01N/27/26 |

OTHER PUBLICATIONS

JPO abstract of Sonoda et al. (JP 64–80852 A).*

Brush, Michael D., "Gel documentation and analysis systems leave a lasting impression", The Scientist, 14[4]:26, Feb. 21, 2000.

Coy, Carol, "Amersham Pharmacia Biotech's IPGphor System separates the headache from 2–D electrophoresis", The Scientist, 14[1]:17, Jan. 10, 2000.

Dose, Eric V. and Georges A. Guiochon, "Internal Standardization Technique for Capillary Zone Electrophoresis," Analytical Chemistry: Spy Dust, 1991, 63, 1154–1158.

Issaq, Haleem J. et al., "A simple two–dimensional high performance liquid chromatography/high performance capillary electrophoresis set–up for the separation of complex mixtures", Electrophoresis 1999, 20, 1533–1537.

Issaq, Haleem J. et al., "Multidimensional high performance liquid chromatography –capillary electrophoresis separation of a protein digest: An update", Electrophoresis 2001, 22, 1133–1135.

Fujiwara, Shigeru et al., "Determination of Cinnamic Acid and its Analogues by Electrophoresis in a Fused Silica Capillary Tube, " Analytical Chemistry: Monitoring Groundwater and Well Water for Crop Protection Chemicals, Jul. 1986, 58, 1811–1814.

* cited by examiner

*Primary Examiner*—Alex Noguerola
(74) *Attorney, Agent, or Firm*—Fish & Richardson P.C.

(57) ABSTRACT

The present invention relates to a method for separating components of a sample. The method includes obtaining a first separation of the sample components along a first dimension wherein the sample components are at least partially resolved, wherein the first separation can be performed in the absence of an electric field applied to the first dimension. An electric field is used to obtain a second separation of the sample components along a second dimension comprising a plurality of substantially isolated volumes. An intensity-time data record is obtained from each of the isolated volumes, the intensity-time data records containing peaks, each peak being indicative of a migration time. The migration time of a first peak is normalized with respect to a migration time of at least a second peak to correct for migration time differences between the isolated volumes.

29 Claims, 16 Drawing Sheets

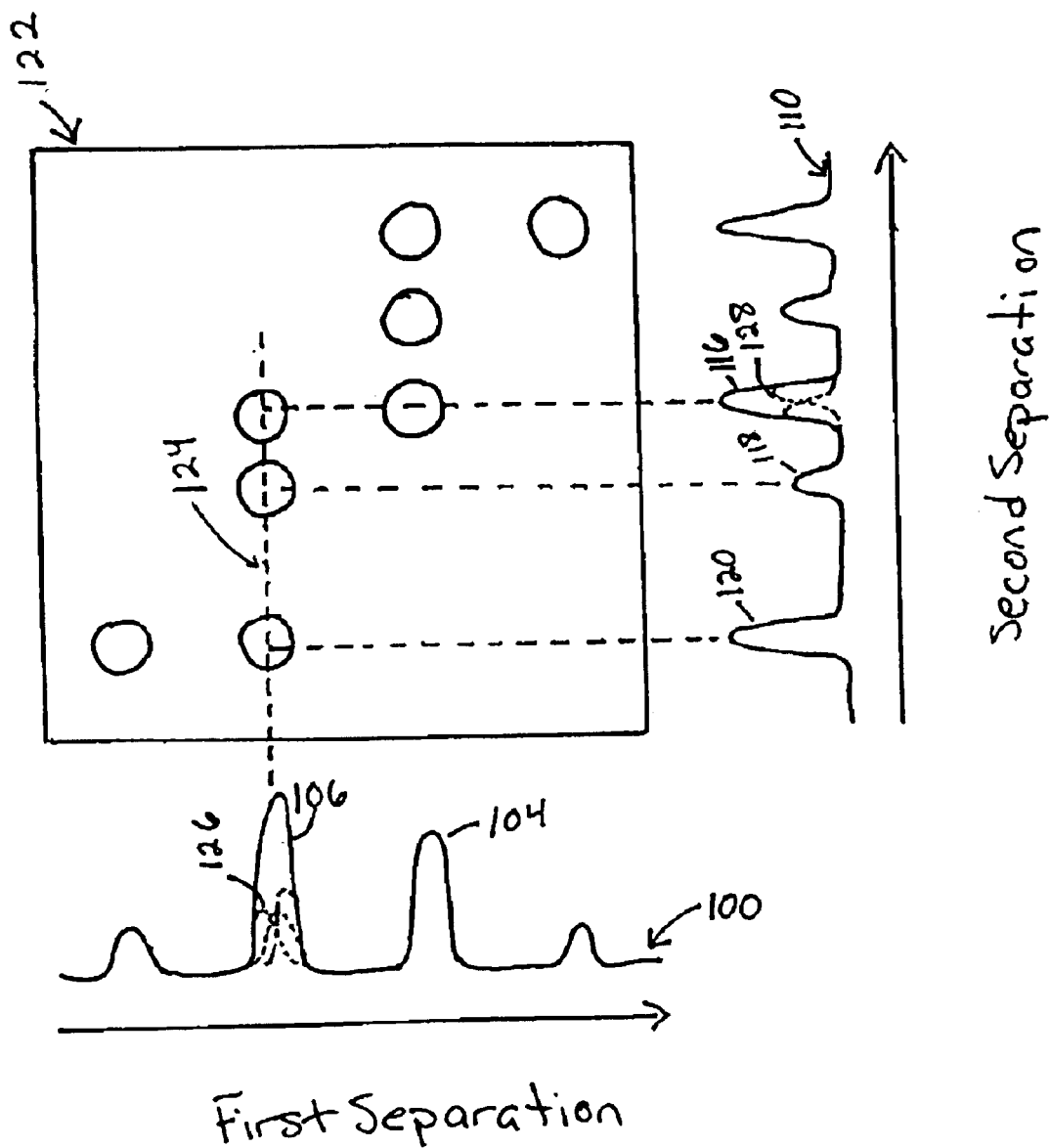

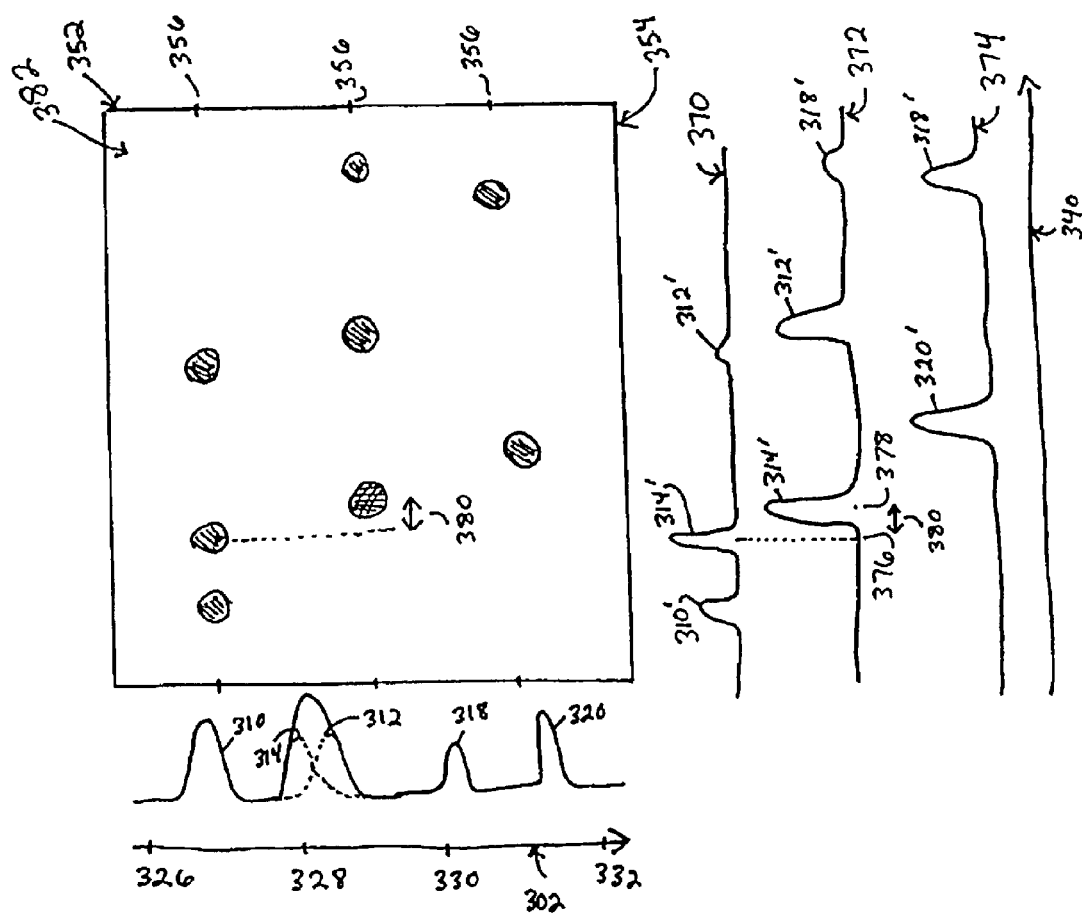

MULTIDIMENSIONAL SEPARATIONS EMPLOYING AN ARRAY OF ELECTROPHORESIS CHANNELS

RELATED APPLICATIONS

This application claims priority to provisional application No. 60/209,588, filed Jun. 6, 2000, and entitled "MULTIDIMENSIONAL SEPARATIONS EMPLOYING AN ARRAY OF ISOLATED ELECTROPHORESIS CHANNELS" which is incorporated herein in its entirety.

TECHNICAL FIELD

An array of electrophoresis lanes is employed as a stage in a multidimensional separation of a sample into its components.

BACKGROUND

Multidimensional electrophoresis, particularly two-dimensional (2D) gel electrophoresis, is a key technology in the analysis of complex samples such as mixtures of proteins. More than ten thousand proteins can be resolved using 2D gel electrophoresis. An example of a gel electrophoresis apparatus using two dimensional electrophoresis is the IPGphor™ system by Amersham Pharmacia Biotech, Piscataway, N.J. Typically, isoelectric focusing (IEF), which separates sample components on the basis of the isolectric point of each component, is used as a first separation dimension. Subsequently, the partially resolved sample from the first dimension, which is generally in the form of a gel strip, is manually attached to a slab gel for the second separation dimension. Such slab gels often separate sample components on the basis of size. Generally, IEF requires about five hours and the slab gel separation requires about six to eight hours to complete.

After the proteins are separated in the slab gel, a dye is used to stain the protein, i.e., at least some of the dye binds to the protein. Unbound dye molecules are washed away using a solvent in a de-staining process. The dye molecules bound to the protein are retained in the gel due to the large binding constant between dye and protein. Then the proteins are detected with a densitometer and digital data is stored in a computer for analysis. The separation and detection procedure and data processing are time intensive, normally requiring about 72 hours to complete. electrophoresis column to analyze the effluent from an HPLC. Such an approach may suffer from significant drift as the electrophoresis column is used to analyze many samples. Additionally, the method requires a tremendous amount of time to analyze the HPLC effluent.

Another example of a multidimensional electrophoresis apparatus is shown in U.S. Pat. No. 6,013,165 to Wiktorowicz, et al. This apparatus includes a first electrophoresis dimension and a second electrophoresis dimension.

Current 2D gel technology includes a number of shortcomings. For example, slab gels allow migrating species travel along curved paths of uncertain length because the migration lanes are not well defined. Migration paths of uncertain length prevent the accurate determination of molecular parameters such as, for example, isoelectric points, molecular identities, mass values, and molecular size, that are estimated from the migration distance. Additionally, errors introduced in slab gel migration complicate data analysis and frustrate automation.

Known techniques have poor sensitivity making it impossible, for example, to quantitatively measure proteins with low natural abundance. Furthermore, the dynamic range of known 2D gel techniques for detecting sample components of different concentrations is limited to about one order of magnitude.

SUMMARY OF THE INVENTION

One embodiment of the present invention relates to a method for separating components of a sample, comprising the steps of obtaining a first separation of the sample components, wherein the first separation can be performed in the absence of an electric field applied to the first dimension and using an electric field to obtain a second separation of the sample components using a plurality of substantially isolated channels.

Preferably, the sample components are at least one of peptides and proteins. In one embodiment, the first dimension comprises an HPLC column and the second dimension comprises a plurality of electrophoresis columns. In another embodiment, the second dimension comprises a substrate defining a plurality of channels.

An intensity-time data record is obtained from each of the isolated volumes. The intensity-time data records contain peaks indicative of the presence of sample components. Intensity-time data records may include, for example, electropherograms and chromatograms. Although certain separative techniques, such as isotachophoresis can provide intensity-distance data records, these records are considered equivalent to intensity-time data because each type of data includes peaks indicative of at least partially separated sample components.

Another embodiment of the invention relates to a method for separating components of a sample, comprising obtaining a first separation of the sample components into a first plurality of sample volumes in the absence of an applied electric field. Sample volumes may include, for example, fractions of eluant from a first separation technique such as HPLC. A simultaneous second separation of sample components present in each of the first plurality of sample volumes is performed in the presence of an electric field. By simultaneous it is meant that the sample components present in any one of the first plurality of sample volumes are separated at substantially the same time as the sample components present in other of the first plurality of sample volumes. The sample components present in different sample volumes are separated in a respective one of a plurality of substantially isolated separation channels. To separate sample components present in a sample volume in a separation channel, at least a portion of the sample volume is introduced or injected into the separation channel. Preferably, portions of different sample volumes are introduced or injected into different separation channels.

An intensity-time data record from each of the isolated channels is obtained. A migration time of a first peak is normalized with respect to a migration time of at least a second peak to correct for migration time differences between the isolated channels.

Another embodiment of the present invention comprises a method for separating components of a sample, comprising obtaining a first separation of the sample components into a first plurality of sample components in the absence of an applied electric field. A simultaneous second separation of each of the first plurality of sample components is obtained in the presence of an applied electric field to thereby form a plurality of substantially isolated volumes from each of said plurality of sample components.

A migration time of at least one of the substantially isolated volumes is normalized with respect to a migration time of at least a second substantially isolated volume to correct for migration time differences between the isolated volumes.

In another embodiment, an intensity of a first substantially isolated volume is normalized with respect to an intensity of at least a second substantially isolated volume to correct for intensity differences between the isolated volumes.

BRIEF DESCRIPTION OF THE FIGURES

The present invention is illustrated below in reference to the following drawings in which:

FIG. 4 illustrates the resolution of overlapped sample components in a multidimensional separation plot;

FIG. 7 illustrates the affect of migration time variation on a two-dimensional separation;

FIG. 12 presents a two dimensional separation plot according to the invention;

FIG. 13 shows a subset of electropherograms from FIG. 10a;

DETAILED DESCRIPTION OF THE INVENTION

Figure 1B:
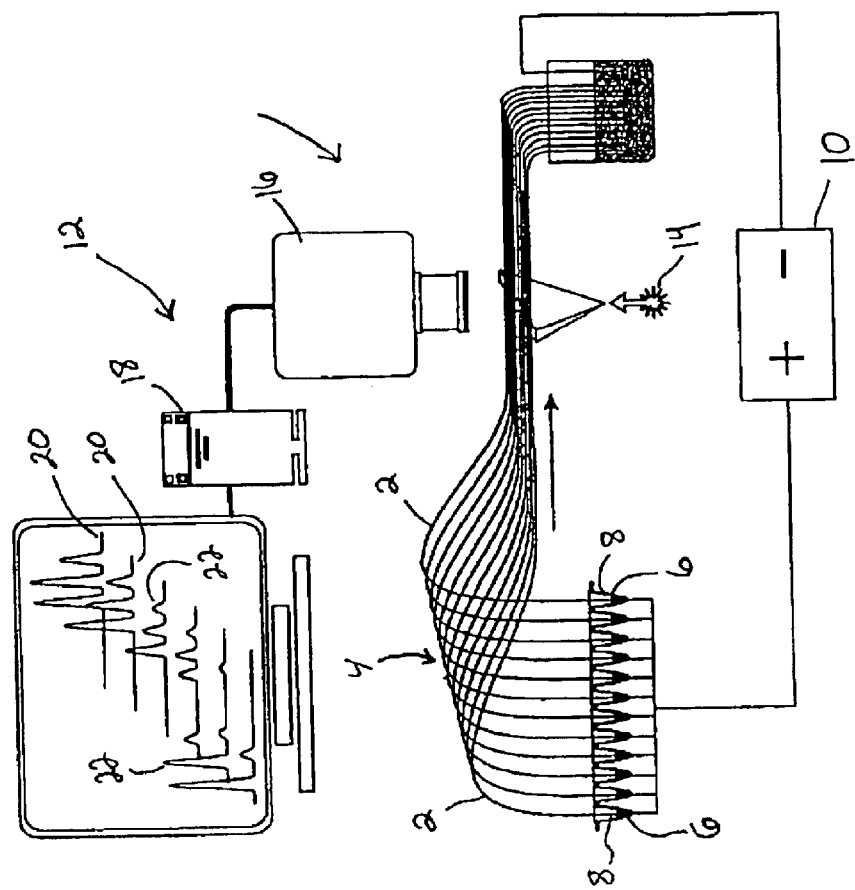
FIGS. 1a and 1b show an embodiment of a multidimensional separation apparatus according to the present invention.

The present invention relates to the use of an array of isolated electrophoresis lanes or channels as a dimension in a multidimensional separation of sample components. The terms lanes or channels are used synonymously herein and refer generally to a structure, such as a capillary or a channel microfabricated in a substrate, configured to support the electrophoretic separation of sample components. By isolated it is meant that sample components are prevented from migrating into an adjacent lane or channel so that sample components from adjacent lanes do not mix. The lanes or channels of the present invention define known migration paths that allow the migration distance of each sample component to be determined with greater accuracy and precision than in a slab gel format where sample components can travel through undetermined, curved paths.

Because sample components are confined within each lane or channel, the components cannot move from one lane to an adjacent lane. Thus, lane tracking is not required to determine accurate migration times of the sample components. In contrast, slab gel electrophoresis requires lane tracking because sample components can migrate into adjacent lanes of the gel. In 2D gel electrophoresis, however, it is not practical to track lanes. Therefore, the protein migration patterns are uncertain in known 2D gel electrophoresis techniques, making these techniques qualitative rather than quantitative techniques.

The array of isolated electrophoresis channels is used to separate a plurality of samples that have been subjected to a first separation. The first separation dimension utilizes at least one of a physical or chemical property of the sample components to effect at least partial separation thereof. Separative techniques that are suitable for the first dimension include, but are not limited to, liquid chromatography, high pressure liquid chromatography, size exclusion chromatography, field flow fractionation, thin layer chromatography, and centrifugation. Preferably, the first separation dimension comprises a separative technique that does not require the application of an electric field to effect a separation. Combining a non-electric field based technique with electrophoretic separations increases the resolving power of the present invention because the sample components are separated on the basis of different physical and chemical properties along each dimension.

The output of the first separation dimension is divided into a plurality of volumes to provide a set of samples for the second separation dimension. Because the sample components are at least partially resolved the abundance of at least one of the sample components varies between the volumes. Thus, merely dividing a sample into a plurality of small volumes in which the abundance of at least one of the sample components does not vary from volume to volume would typically not constitute an initial separation.

Preferably, each dimension of the multidimensional separation utilizes a different property of the sample components to effect a separation. For example, one embodiment of the present invention comprises a first separation dimension of HPLC and a second dimension utilizing an electrophoretic separation technique. Therefore, one of the dimensions, e.g., the capillary number, corresponds to the retention time from the HPLC dimension and is related to the hydrophobicity of the protein molecules. The other dimension, which corresponds to the migration time from the capillary zone electrophoresis dimension, is related to the ratio of the protein charge to the protein cross-sectional area. For example, proteins having a longer migration time tend to have a more negative charge at pH 9.0. Another embodiment of the present invention, which is discussed below, uses a first separation of isoelectrical focusing and a second separation based on protein size using an array of capillary gel electrophoresis channels.

Figure 1A:
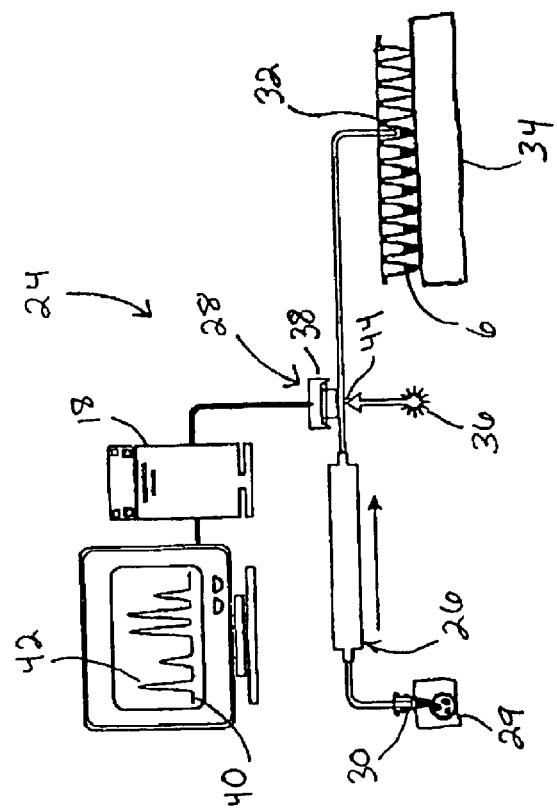
Figure 1A:
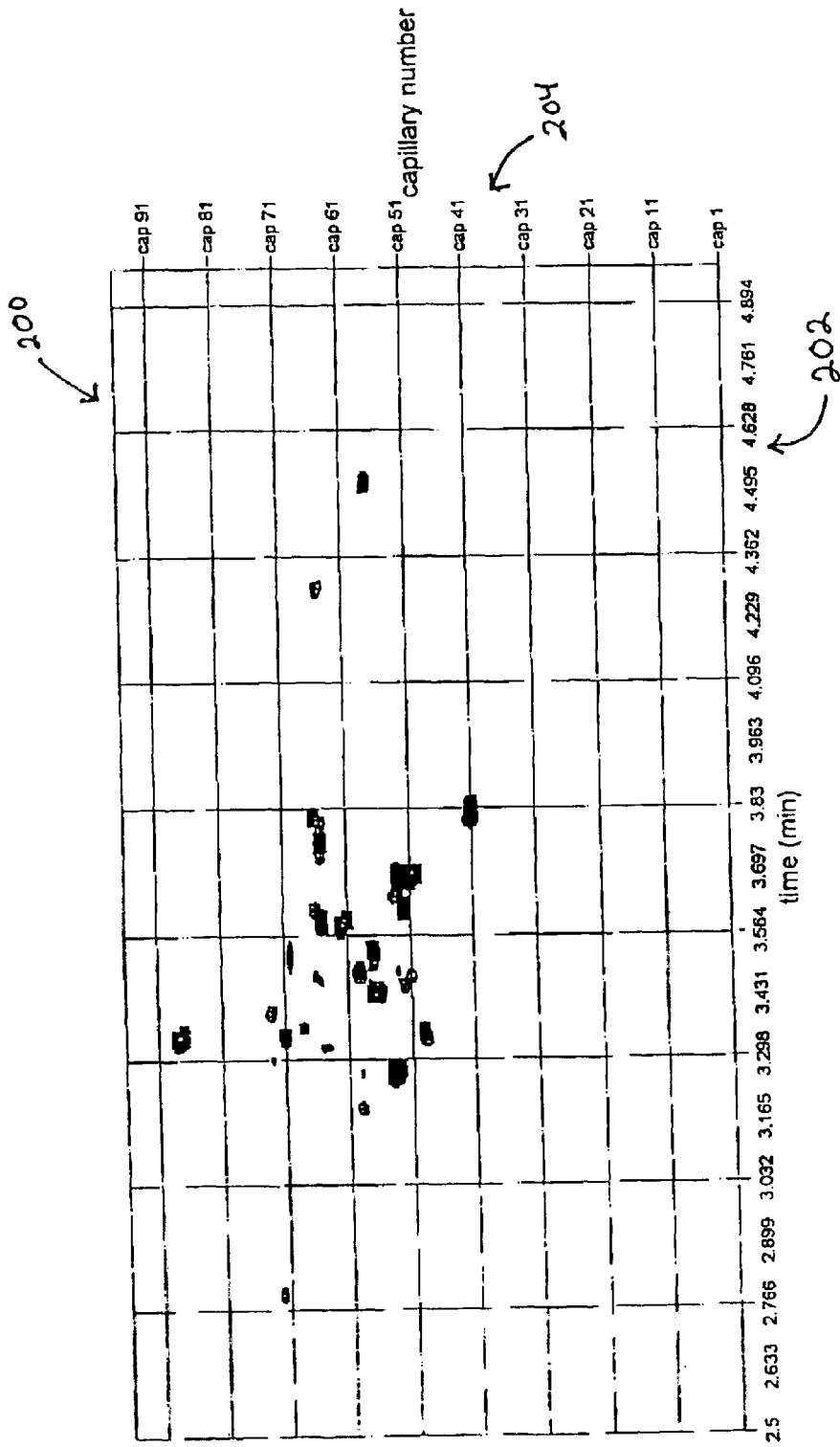

Referring to FIG. 1, the present invention includes an electrophoresis system 1 comprising a plurality of channels defined by capillaries 2, which are configured into an array 4 of channels. In this embodiment, the array of capillaries is the array of isolated electrophoresis channels. Suitable electrophoresis systems are disclosed in, for example, U.S. Pat. No. 5,916,428 to Kane et al. and U.S. Pat. No. 6,027,627 to Li et al., which are hereby incorporated by reference in their entireties. Capillaries 2 are formed of any material suitable for electrophoretic separations, such as silica, glass or polymer, as known in the art. Electrophoresis system 1 includes a power supply 10 to generate an electric field across capillaries 2.

A plurality of samples to be separated are disposed into respective sample introduction wells 6. First ends 8 of capillaries 2 are preferably spaced apart in an array corresponding to sample introduction wells 6, such as the wells of a micro titre tray. Samples provided in wells 8 can be introduced into respective capillaries and subjected to simultaneous separation. Sample component migration begins when the electric field is applied to the channels.

Because different channels of the second dimension are substantially isolated from one another, samples migrating within a given channel separate into substantially isolated volumes. For example, a peak is indicative of the presence of a sample component within a substantially isolated volume of a particular channel.

A detection system 12 is provided to detect the presence of sample components separated in capillaries 2. Detection system 12 preferably includes a light source, such as laser 14 and a detector, such as CCD 16, configured to respectively generate and detect fluorescence from sample components. The detector is preferably in communication with a computer 18, which is configured to process signals from the detector to provide an electropherogram 20 from each capillary 2. A suitable detection system is disclosed in, for example, U.S. Pat. No. 5,998,796 to Liu et al and U.S. Pat. No. 6,118,127 to Liu et al, both of which are incorporated in their entireties by reference. Electropherograms 20 include peaks 22 indicative of the presence and migration time of each sample component. Alternatively, the detection system can be configured to determine the absorbance of the sample components. In this embodiment, the light source is preferably a lamp, such as a mercury lamp or deuterium lamp. Using either fluorescence or absorbance detection, the present invention affords more rapid and sensitive detection than 2D gel electrophoresis techniques, which require pre-detection steps such as staining and destaining. These steps, which are not required in the present invention, can introduce significant quantization errors.

The present invention also provides more sensitive detection over a wider range of concentration levels than does 2D gel electrophoresis. For example, CCD cameras have a dynamic range of 4 orders of magnitude using a 16 bit camera, which far exceeds the one order of magnitude dynamic range of densitometers used to detect sample components in 2D gel electrophoresis.

The electrophoretic separation can include any separation technique comprising the use of an electric field including, but not limited to, capillary zone electrophoresis, isoelectrophoresis, capillary gel electrophoresis, electrophoretic chromatography using open or packed channels, micellar electrophoresis, and isotachophoresis. Some embodiments of electrophoresis, such as gel electrophoresis, require that the channels be filled with a gel, which can be a sieving matrix. On the other hand, capillary zone electrophoresis can be carried out using only a fluid solvent/buffer system to fill the channels. The present invention is equally adaptable to all such embodiments of electrophoresis. Preferred sample components to be separated include proteins, peptides, DNA, and other biological molecules.

Referring to FIG. 1, a preferred embodiment of the present invention includes a high pressure liquid chromatograph (HPLC) 24, which includes an HPLC column 26. Samples are introduced to column 26 via an injector 29 at an injection port 30 and flow in a suitable solvent through column 26 toward an output end 32. Volumes of solvent eluting from output end 32 are collected into sample wells 6. As discussed below, each collected volume of solvent is a fraction. HPLC 24 preferably includes an autosampler 34 configured to position output end 32 relative to sample wells 6 such that each sample well receives a respective fraction of the total output from output end 32. Computer 18 includes a processor configured to determine the volume of reach fraction and the rate at which different fractions are obtained. In one embodiment, the fractions obtained from the first separation dimension are arranged in a micro titer tray, preferably having a plurality of rows and columns, such as 8×12 or 16×24.

HPLC 24 includes a detection system 28 configured to detect sample components at detection zone 44 in column 26. Detection system 28 preferably includes a light source 36 and a detector 38. Preferably, detection system 28 is configured to detect at least one of sample component absorbance and fluorescence. Alternative detection techniques, such as electrochemical detection can also be used.

Detector 38 is in communication with a computer 18 configured to process signals from the detector to provide a chromatogram 40, which includes peaks 42 indicative of the presence and retention time of detected sample components. A sample component's retention time is defined as the period of time required for the sample component to reach detection region 44 after a sample is introduced to column 26.

The electrophoresis apparatus in FIG. 1b and the HPLC apparatus in FIG. 1a can be combined in a modular system comprising each apparatus. In this embodiment, it is preferred that the system be controlled by a single computer. Alternatively, an electrophoresis apparatus and an HPLC apparatus could be linked by a robotic sampler configured to provide the fractions collected from the first separation to the input end of the separation channels of the electrophoretic apparatus. Direct coupling of the two apparatuses or robotic sampling is not required. Samples can be transferred manually from the first separation to the second.

The present invention provides a tremendous reduction in sampling time gained by the present invention. For example, consider collecting fractions from chromatographic column 26 into a plurality of sample vials 6. A chromatographic separation generally requires from about 10 to 20 minutes to accomplish. Subsequently, the fractions in the vials 6 are analyzed using electrophoresis separation apparatus 1 having 96 capillaries 2. A single initial sample is turned into 96 separated sub-samples in a time of about 20–30 minutes. The 96 subsamples are analyzed in 1 run using 96 electrophoretic channels for a total time of about 20 to 30 minutes. Using a single electrophoretic column would require more than about 960 minutes or at least about 50 times as long as the array based approach of the present invention.

Figure 2:
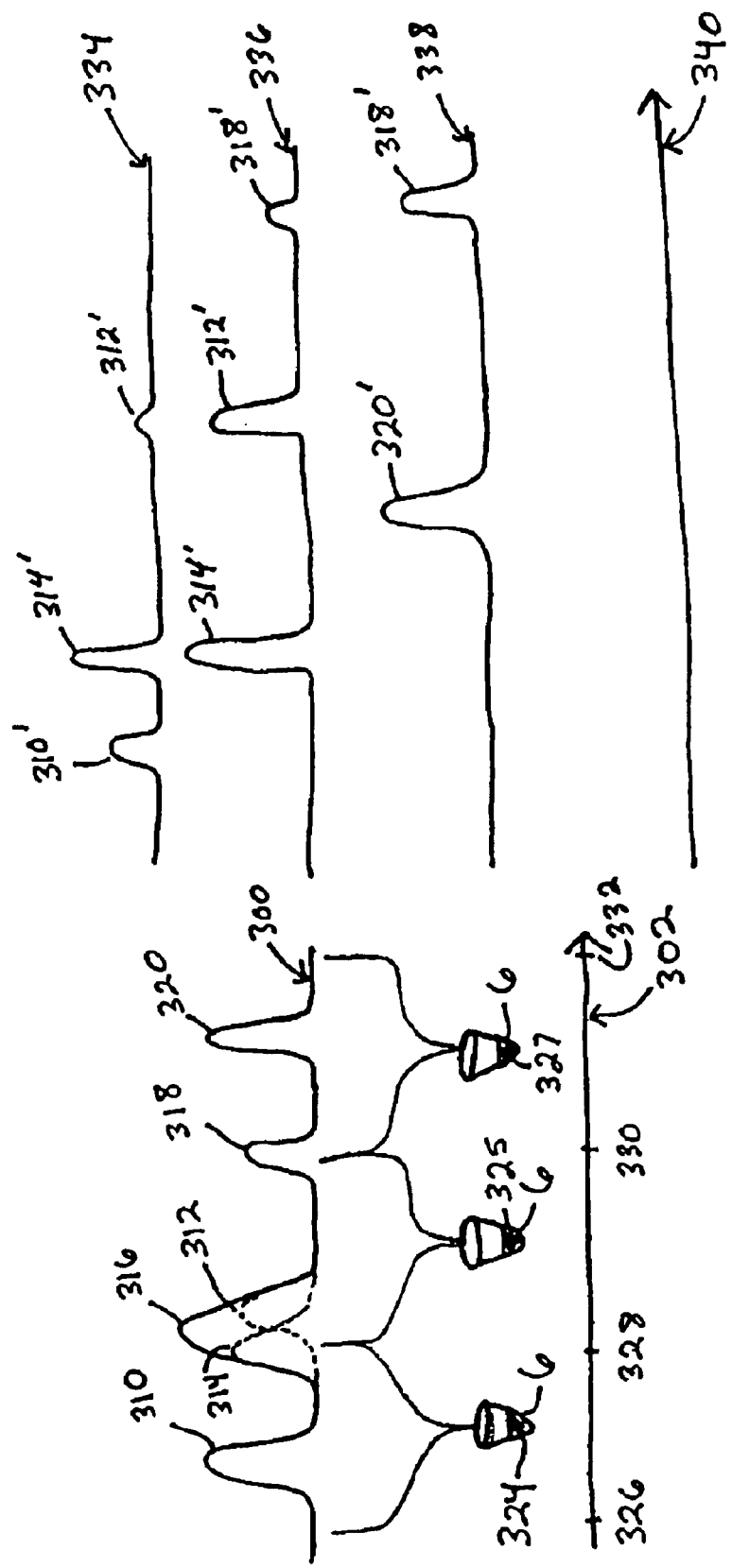
FIG. 2 illustrates the collection of fractions from a first separation dimension.

FIG. 2 shows a chromatogram 300 having peaks 310, 316, 318, and 320, which elute at different retention times along retention time axis 302. Each peak is indicative of the presence of one or more sample components. Peak 316, for example, is formed by the presence of two partially overlapping peaks 312 and 314. Successive fractions of eluant, each comprising eluant collected over a range of retention times, are collected into sample vials or wells 6, preferably belonging to the afore-mentioned micro titre tray. A fraction 324, for example, includes eluant collected from a retention time 326 to a later retention time 328. Fraction 324 contains contributions from sample components 310, 312, and 314. Fraction 325, on the other hand, contains eluant collected from retention time 328 to a later retention time 330 and fraction 327 contains eluant collected from retention time 330 to a later retention time 332. It should be understood that the collection of eluant fractions and formation of a two-dimensional separation plot does not require detecting the partially separated sample components in the first separation dimension.

Each fraction collected from the first separation dimension provides a sample for separation in a channel of the second separation dimension. For example, after chromatography, fractions 324, 325, and 327 are analyzed in respective channels of an electrophoretic separation dimension providing electropherograms 334, 336, and 338, respectively. Each electropherogram includes peaks indicative of the presence of sample components. The peaks also indicate the migration time of the sample components along a migration time axis 340. Because fractions 324 and 325 each contain contributions from the sample component indicated by peak 314, electropherograms 334 and 336 each contain a peak 314' indicating the presence of that component.

The migration time behavior of components in the electrophoretic dimension is different from the retention time behavior of components in the chromatographic dimension. Therefore, peaks that were overlapped in one dimension can generally be resolved in the other dimension. For example, electropherograms 334 and 336 include resolved peaks 312' and 314' that correspond to overlapped peaks 312 and 314 in chromatogram 300.

Figure 3:
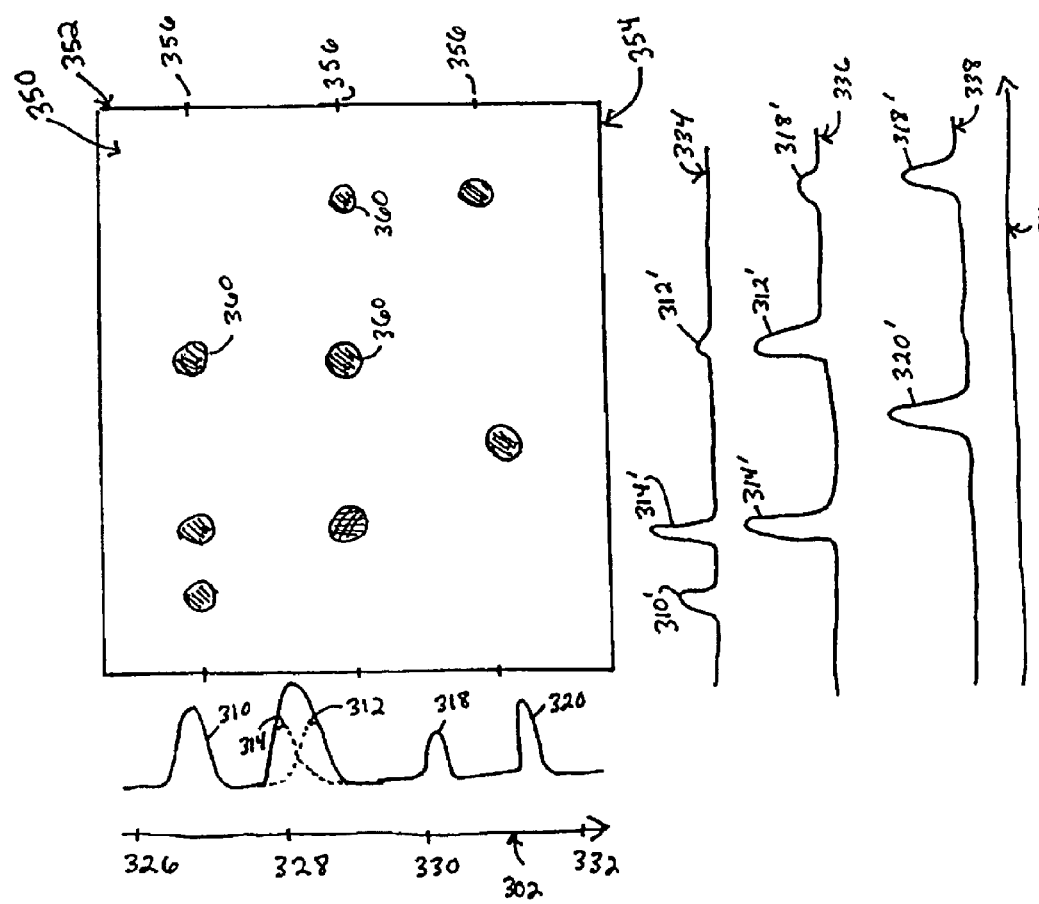
FIG. 3 illustrates the construction of a multidimensional separation plot from a first and second separation dimension.

FIG. 3 illustrates how a two-dimensional separation plot 350 is constructed upon separating fractions 324, 325, and 327 in respective electrophoretic separation channels. A plurality of rows 356 along a first axis 352 of separation plot 350 correspond to individual electropherograms obtained from successive fractions collected from the first separation dimension. Because each fraction can be related to a corresponding retention from the first separation dimension, each row 356 corresponds to a different retention time from the first separation dimension. A second axis 354 of separation plot 350 corresponds to migration time axis 340. Separation plot 350 includes a plurality of features 360 that correspond to peaks obtained in each electropherogram.

FIG. 4 shows a separation plot 122 to illustrate that the combination of two separation dimensions completely resolves sample components even if neither dimension alone completely resolves the components. This is because sample components that overlap in one of the dimensions will generally exhibit different migration or retention behavior in the other dimension. For example, line 124 shows that a peak 106 from a chromatogram 100 comprises contributions from three overlapped components 126. The three overlapped components 126, however, do not overlap in an electrophoresis dimension 110 because the three overlapped peaks 126 are resolved as peaks 116, 118, and 120. Similarly, peak 116 of electropherogram 111 is composed of two overlapped peaks 128. In chromatogram 100, however, overlapped peaks 128 are resolved as a peak 104 and peak 106.

In some cases it may be desirable to modify the sampling rate while collecting the output of the first dimension. For example, if one range of retention times is known or predicted to contain a large number of partially resolved sample components, the sampling rate could be increased to enhance the informing power gained by adding the second dimension. Alternatively, if a range of retention times is known to contain few sample components, the sampling rate could be decreased to most efficiently use the second dimension.

Figure 5A:
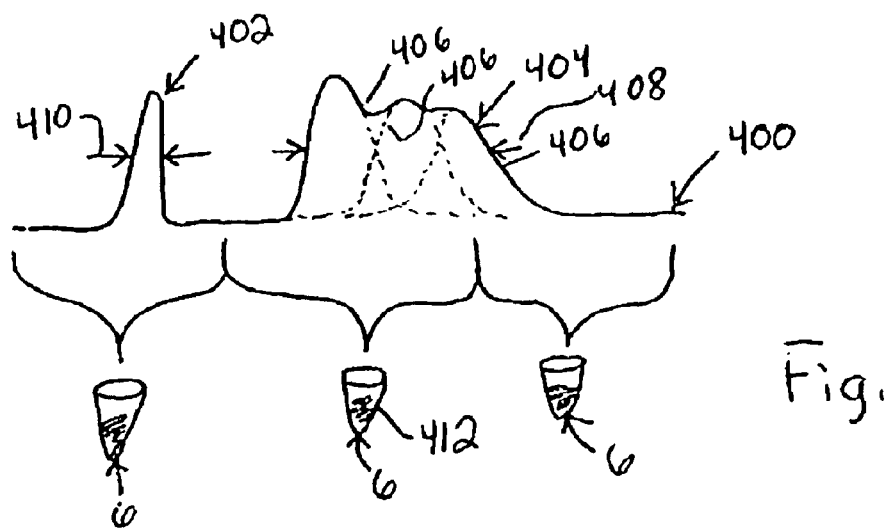
FIGS. 5a and 5b illustrate the collection of varying sample fraction volumes according to the invention.

Referring to FIG. 5a, a chromatogram 400 includes a peak 404, which comprises contributions from several underlying peaks 406. Underlying peaks are only rarely completely overlap one another. Therefore, peak 404 is broader than a peak 402, which includes contributions from only one component peak. The broader width of peak 404 can be quantified by arrows 408, which show that the width at one half maximum intensity of peak 404 is greater than the width at one half maximum intensity of peak 402, shown by arrows 410.

Because peak 404 comprises contributions from a plurality of sample components, there is an increased probability that one or more of peaks 406 will also overlap when subjected to separation along the second separation dimension. Peaks that overlap one another along both separation dimensions cannot be fully resolved into separate components. Therefore, in one embodiment of the present invention, the detector signal from the first separation dimension is used to determine whether overlapping peaks are likely to be present. If the possibility of overlapping peaks is indicated, the volume of eluant collected into each fraction is reduced. This decreases the number of sample components that are likely to be present in each fraction, which also decreases the probability of overlapping peaks when the fractions are separated in the second separation dimension.

Figure 5B:
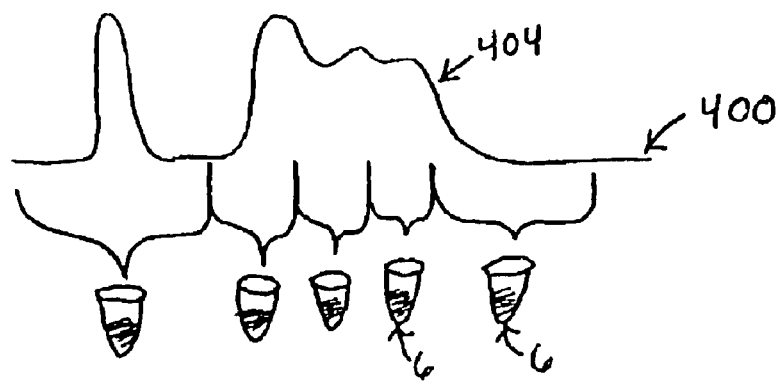
Figure 6:
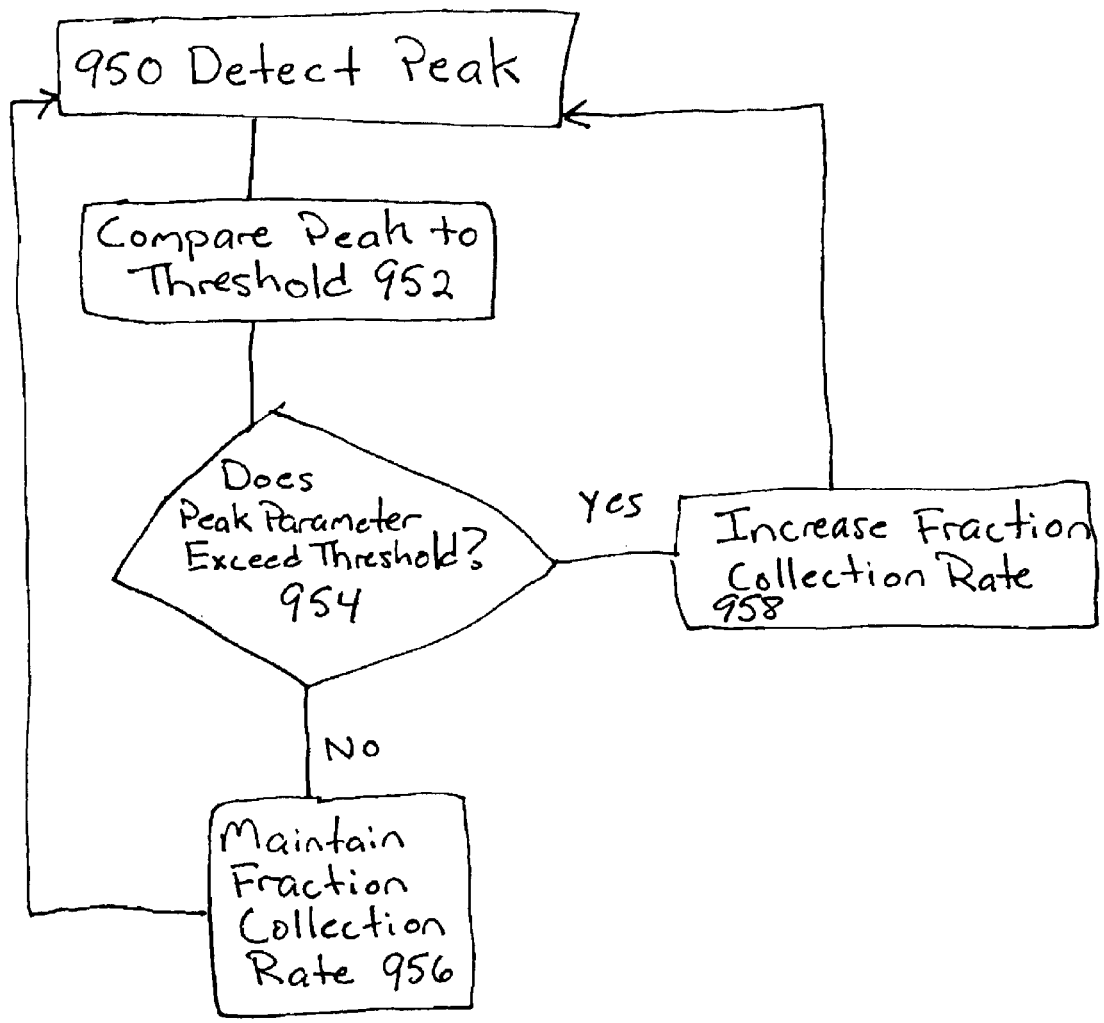
FIG. 6 is a flow chart illustrating process steps for the collection of varying sample fraction volumes.

Referring to FIG. 6, computer 18 preferably includes a processor, software or code stored in memory that is configured to detect 950 the presence of overlapping peaks by identifying peaks having a width greater than surrounding peaks. In step 952, the width of the peak is compared to a threshold value. For example, the threshold value can be based upon the width of the most recent previous peak. Upon identifying 958 a peak having a greater width than surrounding peaks, computer 18 actuates autosampler 34 to increase the rate at which fractions are collected. This can be done by, for example, increasing the rate at which successive sample wells 6 are positioned to receive eluant from output end 32. Referring to FIG. 5b, autosampler collects successive fractions 414, 416, and 418, each of which has a smaller volume than a fraction 412. The increased sampling rate preferably continues until sample components contributing to the wide detected peak are essentially fully collected in fractions. If the width of the detected peak does not exceed the threshold, the fraction collection rate is maintained in step 956.

As discussed above, fractions containing partially resolved sample components from the first separation dimension are subjected to separation in different channels of the second separation dimension. Different channels of the second separation dimension, however, do not always provide identical separation performance. Thus, the same sample component will produce different migration times when separated along different channels of the second separation dimension. FIG. 7, for example, shows a separation plot 382 that results when fractions 324, 325, and 327 are separated in second dimension channels that do not provide identical separation performance. Peak 314' appears at a migration time 376 in an electropherogram 370 and at a different migration time 378 in an electropherogram 372. A migration time error is shown by arrows 380. The migration time error 380 also appears in separation plot 382.

To correct migration time errors, a reference sample is added to each fraction to be separated in the second separation dimension. In the absence of migration time differences between channels, each reference peak will exhibit the same migration time in different channels. Because migration time variations between channels will affect all peaks within an electropherogram, the migration time of a reference sample peak in an electropherogram can be used to normalize the migration times of the other peaks in each electropherogram. Normalization removes channel-to-channel migration time variations from the migration time data, allowing the migration times of peaks in one channel to be compared to the migration times of peaks in a different channel.

Figure 8A:
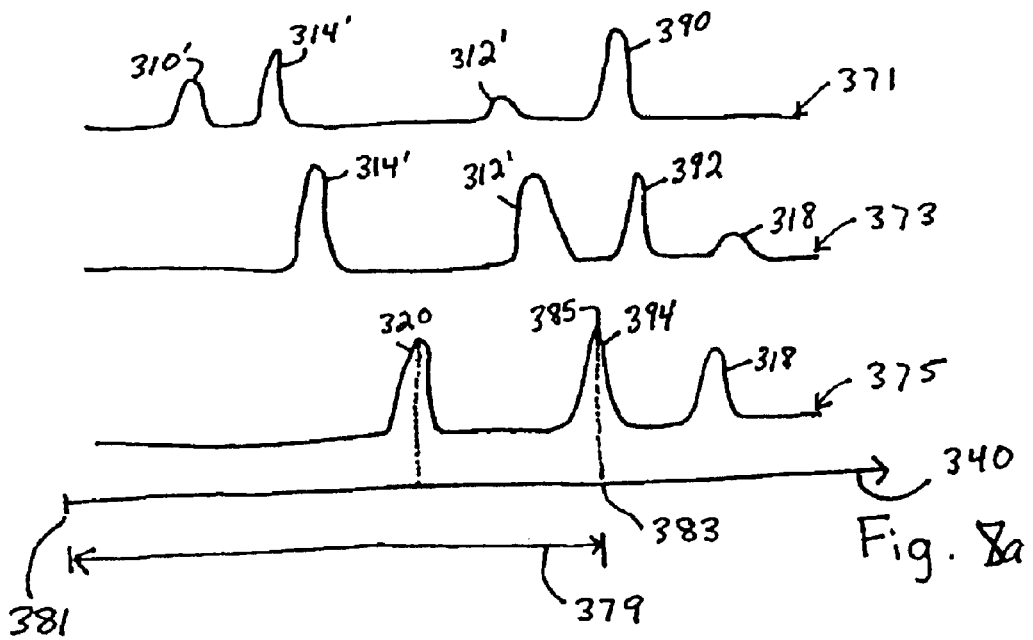
FIGS. 8a and 8b illustrate the use of reference sample peaks to correct migration time variations in two-dimensional separations according to the invention.

FIG. 8a shows electropherograms 371, 373, and 375 that result when fractions 324, 325, and 327 are each separated in one of three different electrophoresis channels after a reference standard has been added to each fraction. The reference sample peaks appear as peaks 390, 392, and 394. Computer 18 includes software or executable code stored in memory that is configured to use the migration times and intensities of the reference peaks within each channel to normalize the migration times and peak intensities of the peaks of other sample components within the same channel.

Normalization preferably begins by identifying the reference peak within each electropherogram. If more than one reference peak is used in a channel, the different reference peaks can also be discriminated from one another. For example, each reference sample can be arranged to fluoresce at a different wavelength from the other samples in a channel. Using a two-dimensional detector, the fluorescence from the reference sample peaks can be discriminated from the fluorescence of other sample peaks. If more than one reference sample is used in each channel, the different reference samples are configured to fluoresce at different wavelengths. Alternatively, the reference sample peak can be arranged to absorb light at wavelengths different from peaks of the other sample components. Computer 18 is configured to identify each reference peak based upon the detected signal.

After identifying the reference peak in a channel, the migration time t of each peak and the migration time $t_{ref}$ of each reference peak is determined. The migration time is preferably defined as the length of time required for a sample component to migrate between the sample introduction end of the capillary and the detection zone. For example, to determine the migration time of reference peak 394, computer 18 is configured to determine the amount of time 379 between a time 381 the electric field is applied to the channels and a time 383 that reference peak 394 is detected. To determine the detection time of a peak, computer 18 preferably determines the time corresponding to a maximum intensity 385 of peak 394. Migration times for other peaks are determined in a similar fashion. The normalized migration time for each peak is determined by computer 18 as $t_n=t/t_{ref}$.

Figure 8B:
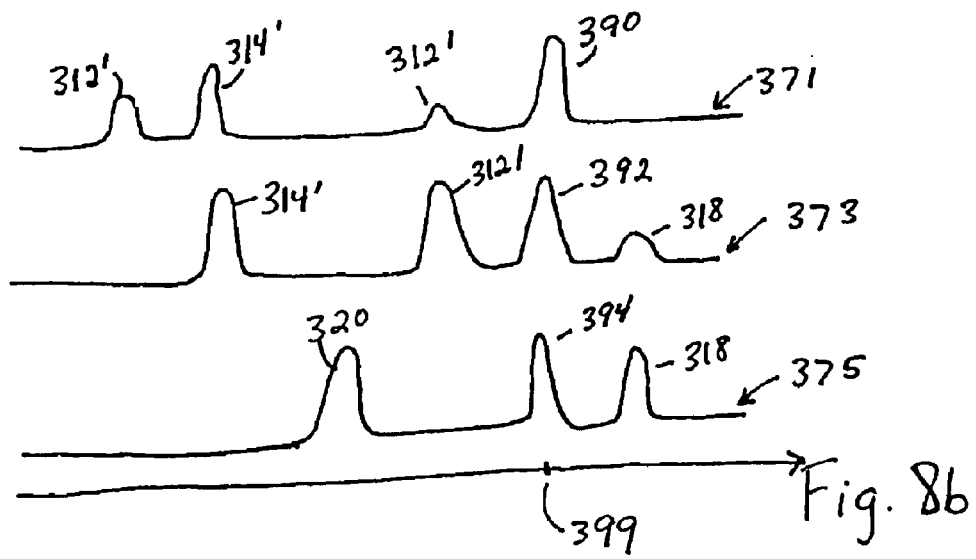

Computer 18 is also configured to determine a corrected migration time $t_c$ of each peak. The corrected migration time uses the average migration time $t_{ref_{ave}}$ determined from a plurality of reference samples. Computer 18 identifies the reference peaks in the different channels and determines the average migration time. Computer 18 then uses the average migration time to correct the normalized migration time of each peak so that it corresponds to the migration time that would have been observed in the absence of channel-to-channel migration time differences. The corrected migration time is preferably determined by taking the product of the normalized migration time $t_n$ and the average reference peak migration time $t_{ref_{avg}}$ or $t_c=t/t_{ref} \times t_{ref_{ave}}$. FIG. 8b shows that after normalization and correction, reference sample peaks 390, 392, and 394 are aligned at a migration time 399 along migration dimension 340, thereby also adjusting the sample peaks to a common index. Other peaks in each channel are adjusted to migration times that are relative to the reference sample peaks. The relative migration times of a sample component and a reference sample should be independent of migration time variations. Thus, normalized or normalized and corrected migration times from peaks in one channel can be compared to those from another channel.e Normalization and correction of migration time can also be performed using a plurality of reference samples within each separation channel. Including additional reference samples allows for normalization and correction of channel-to-channel migration time variations that change as a function of time rather than remaining constant during a given separation. Preferably, the references can be distinguished based upon the wavelength of fluorescence of each reference. When at least two reference samples are used, computer 18 is configured to fit the migration times the reference samples within each channel to a linear or quadratic function. Linear and quadratic interpolation are used to normalize the migration times of other peaks within each channel based upon the parameters estimated from the linear or quadratic fit. When three or more reference samples are used in each channel, cubic spline interpolation is preferred.

A similar normalization process can be used to correct for variations in sample size and detection efficiency between different channels of the second dimension. Each fraction to be separated preferably contains the same concentration of added reference sample. Thus, in the absence of variations between channels the reference sample peaks will have the same intensities. The intensity of a peak is indicative of the abundance of the sample component corresponding to the peak. Computer 18 is configured to determine the intensity of each peak. Preferably, the intensities are determined by integrating the area under each peak. The normalized peak intensity of a peak is given by $A_n=A/A_{ref}$, where A is the peak intensity and $A_{ref}$ is the intensity of the reference peak. If two or three internal standards are used, the intensities are calculated with a polynomial function to correct for channel-to-channel intensity and sampling variations. If more than 3 internal standards are used, a cubic Spline function is preferably used to normalize the intensities of peaks in each channel.

A corrected peak intensity is found by determining the product of the normalized peak intensity and an average peak intensity $A_{ref_{ave}}$ of reference samples in different channels $A_n=A/A_{ref} \times A_{ref_{ave}}$.

Figure 9:
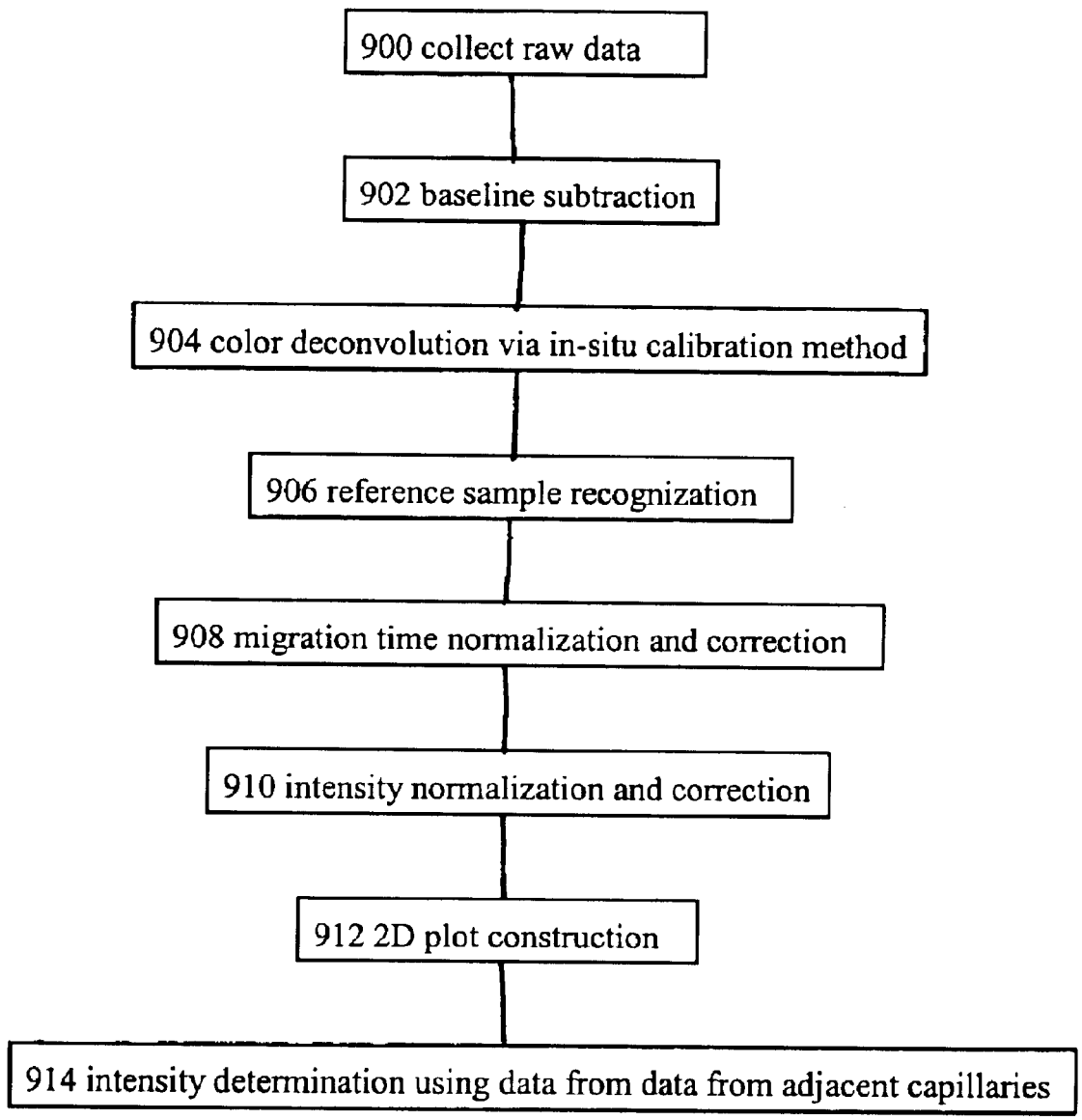
FIG. 9 is a flow chart illustrating process steps for correcting channel-to-channel variations in two-dimensional separations according to the inventions.

Referring to FIG. 9, normalization and correction preferably begin with raw data 900 from the isolated separation channels. Baseline subtraction 902 can be performed to remove any drift from the baseline. Sample peaks corresponding to different fluorescent dyes are preferably deconvolved 904 using in-situ calibration method to discriminate different peaks from one another. Sample references are recognized or identified 906, preferably on the basis of fluorescence wavelength. Migration times are normalized and corrected 908. Intensities are normalized and corrected 910. A 2D plot can be constructed 912 of the separation data. Data from adjacent capillaries is used 914 to determine the total intensity of corresponding to each sample component. For example, FIG. 8b shows that peaks 314', which correspond to the same sample component present in different separation channels, appears in channel 371 and 373. To determine the total amount of the component corresponding to peaks 314', step 914 comprises integrating the intensities of corresponding peaks from different channels.

The steps for normalizing the peak areas or peak migration times can be performed in any order. For example, the reference sample peaks can be identified after determining the peak migration times or peak areas rather than before as described above. Preferably, however, the normalization of migration time is done prior to that of peak areas.

The present invention is not limited to two dimensions and can also be used, for example, with a second electrophoresis dimension such a isolectric focusing in which proteins are resolved on the basis of their isoelectric points or charges. Subsequently, the partially resolved proteins could be separated on the basis of size in an array of electrophoresis channels utilizing SDS-capillary gel electrophoresis.

In another embodiment of the present invention, the first separation dimension comprises isoelectric focusing (IEF), in which sample components are separated based on the migration of the components in a pH gradient until each component reaches its isoelectric point (pI). The pH gradient is preferably established by subjecting an ampholyte solution containing a large number of different-pI species to an electric field, usually in a crosslinked matrix. Analytes added to the equilibrated ampholyte-containing medium will migrate to their isoelectric points along the pH gradient. Although both isoelectric focusing and electrophoresis utilize an electric field, the two separation methods depend on independent properties (net charge and mass) of the sample components. Thus, the combination of one technique with the other enhances the overall resolving power.

Figure 10:
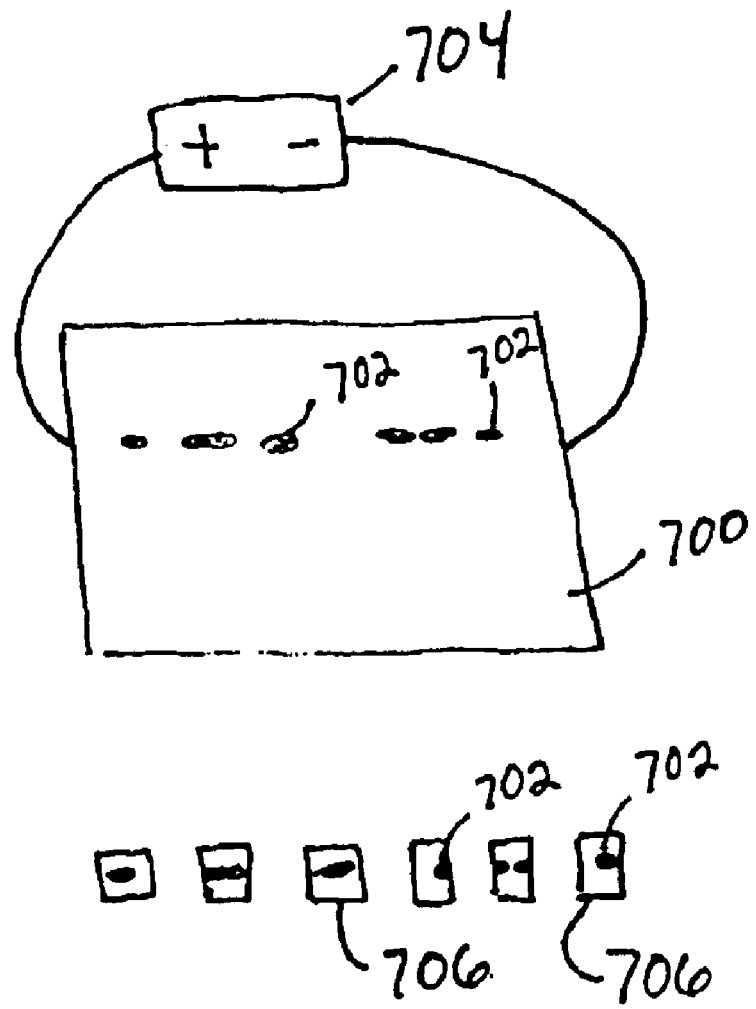
FIG. 10 shows a second embodiment of an isoelectric focusing separation as a first separation dimension according to the invention.

Referring to FIG. 10, a sample comprising sample components 702 is first separated by IEF in a tube or strip gel 700, which includes a power supply 704 to generate an electric field across the gel 700. Next, the gel 700 containing the separated sample components is divided into fractions 706. As described above, each fraction contains contributions from varying amounts of the different sample components. The sample components present in each fraction are separated from the isoelectric focusing gel, such as by vortexing each fraction with a buffer. If fluorescent detection is to be used, the sample components can be derivatized with a fluorescent dye. The sample components from each fraction are then placed in sample vials 6 and subjected to a second separation along a separation dimension comprising an array of isolated electrophoresis channels, such as shown in FIG. 1b. As discussed above, a sample reference can be added to each fraction to correct the migration time and intensity of the peaks resulting from the second separation.

Figure 11:
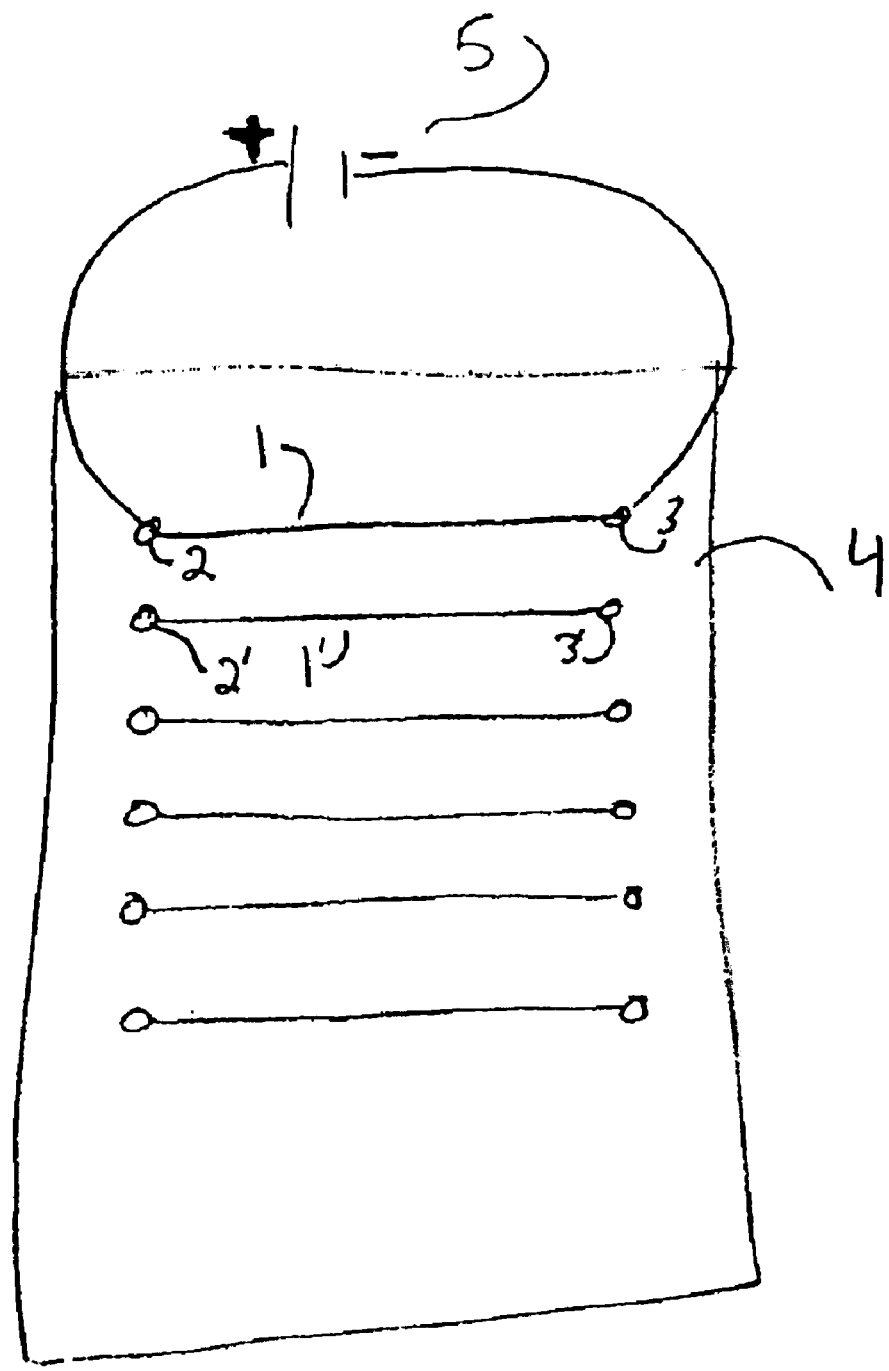
FIG. 11 present an embodiment of an array of isolated electrophoresis channels according to the invention.

As an alternative to capillaries, substantially planar structures can also be used for the second separation dimension. FIG. 11 shows an example of a plurality of lanes 1, fabricated in a planar substrate 4, and containing an array of lanes 1 or channels. Each lane includes means, such as a power supply 5, to establish an electric field across the lane. For clarity, only one lane is shown as being connected to power supply 5. It should be understood, however, that an electric field is preferably established along each lane. The lanes also include a sample reservoir 2 and a waste reservoir 3. Samples are introduced to a separation lane via sample reservoir 2 and, under the influence of the electric field generated by power supply 5, migrate toward waste reservoir 3.

Microfabrication techniques known in the art can be used to fabricate an array of lanes of lanes or channels in a substrate such as glass, silicon, or a polymer. Individual lanes of an array would be defined, for example, by walls of glass, silicon, or polymer to prevent the molecules from migrating into adjacent lanes. The lanes could be sealed with a cover layer to form a structure suitable for supporting electrophoresis according to the present invention.

EXAMPLES

Multidimensional separations according to the present invention are further illustrated in the following non-limiting examples.

Example 1

The following example illustrates the multidimensional separation of protein samples:

Cytochrome c and myoglobin were dissolved in 50 mM Tris-Cl, pH 8.5. by adding trypsin solution (10 mg/mL) with a volume ratio of 20:1. The solution was digested at 37° C. for 18 hours. The protein was labeled with FITC (fluorescein-isothiocyanate) (5 mM) at 37° C. for 30 minutes. All of the chemicals were purchased from Sigma (St. Louise, Mo.).

HPLC Separation

A 100 $\mu$l aliquot of the protein mixture was injected into an HPLC instrument (LIP-1090, Hewlett Packard, Calif.) having a Vydac ODS C18 HPLC column having an inner diameter of 4.6 mm and a length 250 mm, HPLC column. The solvent (acetonitrile and TFA) were used at a flow rate of 1 mL/min. Eluant from the HPLC was fractionally collected into a into 96-well micro titer tray with a microsample collector from ISCO (Lincoln, Nebr.) at 30 second intervals.

Capillary Electrophoresis

The samples in the 96-well micro-titer tray were injected into a HTS-9610 capillary instrument, Spectrumedix, State College, Pa., using vacuum injection at a pressure of −0.5 psi for 10 sec. The running voltage was 13 kV. The 96-capillary cartridge had a total length of 52 cm and an effective length of 35 cm. The capillaries, from Polyrmicro Technologies Inc. (Tuson, Ariz.), had an ID of 50 $\mu$m and an OD of 150 $\mu$m. Optical windows in the capillaries were burned with hot wire. The CE separation buffer included 20 mM borate at pH9.0.

FIG. 12 shows a 2-dimensional plot 200 showing the resulting data. A first axis 202 of 2-dimensional plot 200 corresponds to the migration time of the sample components in the second, electrophoretic dimension. A second axis 204 corresponds to the number of each capillary in the 96 capillary array. As discussed below, the data in FIG. 12 has been time and area normalized in reference to a reference sample present in each capillary.

The present invention allows more rapid, higher resolution separations to be performed than with conventional systems. For example, an HPLC column, the Vydac ci 8 column from Resolution System (Holland, Mich.) was used to separate the protein mixture in 30 minutes. After fractionally collecting the partially resolved protein sample into 96-wells, i.e., fractions, the samples were injected directly into an array of 96 capillaries. The capillary zone electrophoresis separation required a total of about 5 minutes. The analysis time required about 1 minute with a 500 MhZ computer from Dell Computer Corporation. Therefore, the entire 2D separation can be accomplished in less than one hour.

Figure 13:
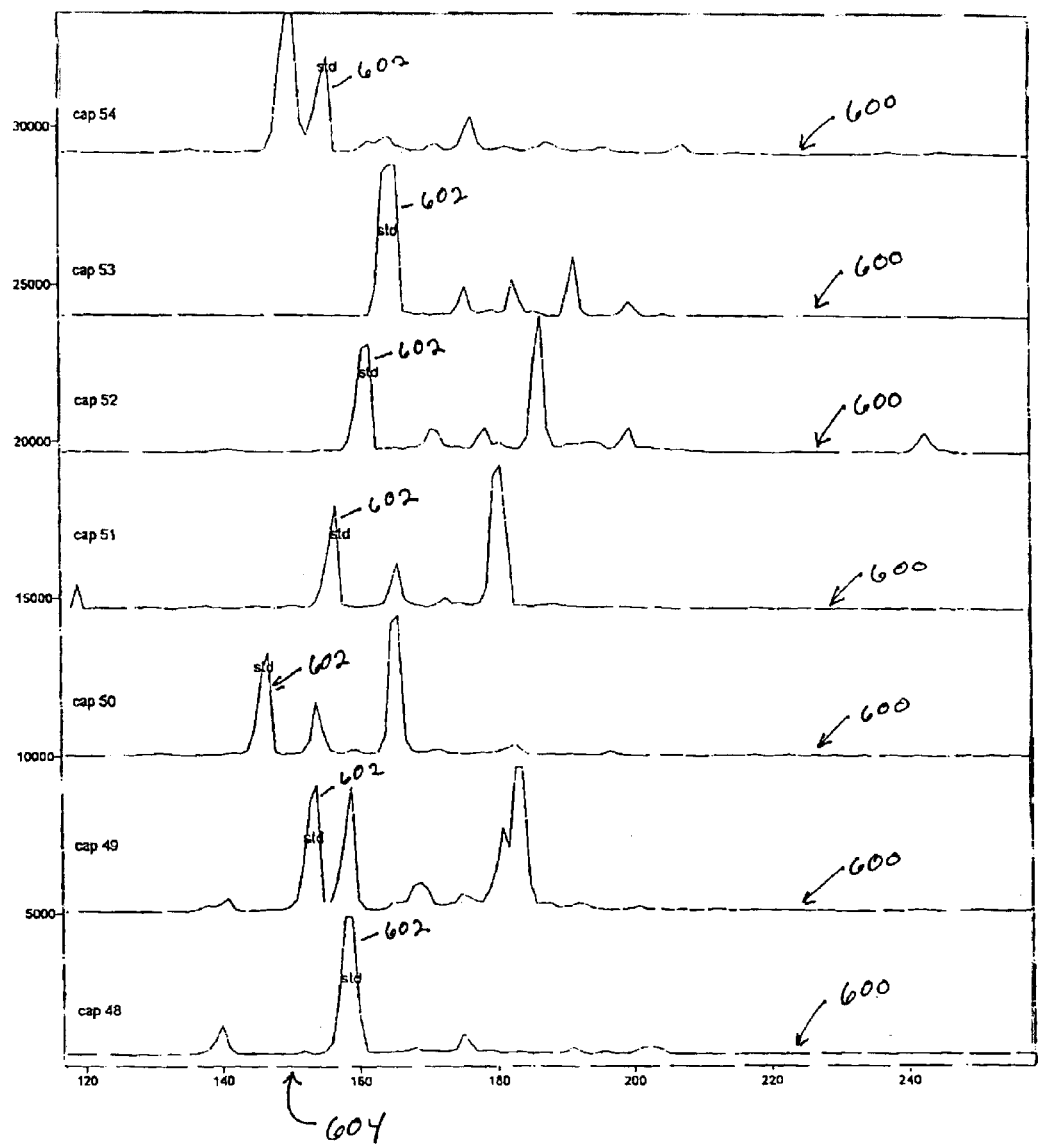

FIG. 13 shows a subset of electropherograms 600, those taken from capillaries numbered 48 to 54. As discussed above, a reference sample was added to each fraction prior to the second separation dimension. Each electropherogram includes a reference sample peak 602. Because of channel-to-channel variations, reference sample peaks 602 appear at different times along migration time axis 604.

Table 1 shows improvement in precision obtained by using the reference sample normalization technique of the present invention. Two dyes (fluorescein and food dye red) were analyzed in the 96-capillary array. The concentrations of each dye in the 96-sample tray are identical. As shown in Table 1, the relative standard deviation of the migration time improves by about an order of magnitude when reference sample normalization is used.

TABLE 1

RSD of the experiments over five trays of 96-capillary run

|  | Reference | Sample | Corrected Sample |
| --- | --- | --- | --- |
| Migration time | 1.61% | 1.67% | 0.12% |
| Peak area | 23.1% | 22.0% | 6.17% |
| Peak height | 21.2% | 21.2% | 13.7% |

Figure 14A:
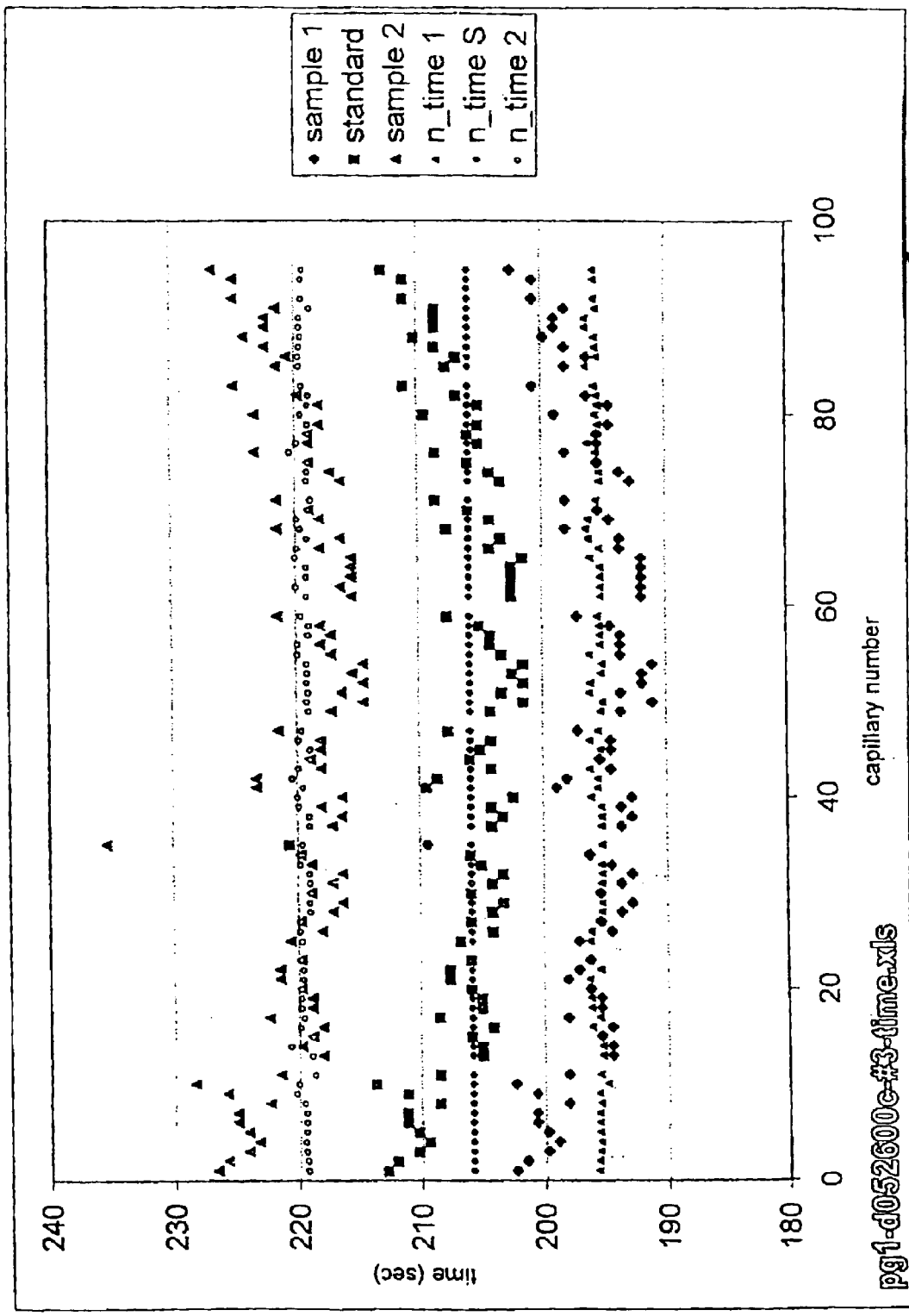
FIG. 14a illustrates the increased migration time precision achieved according to the present invention.
Figure 14B:
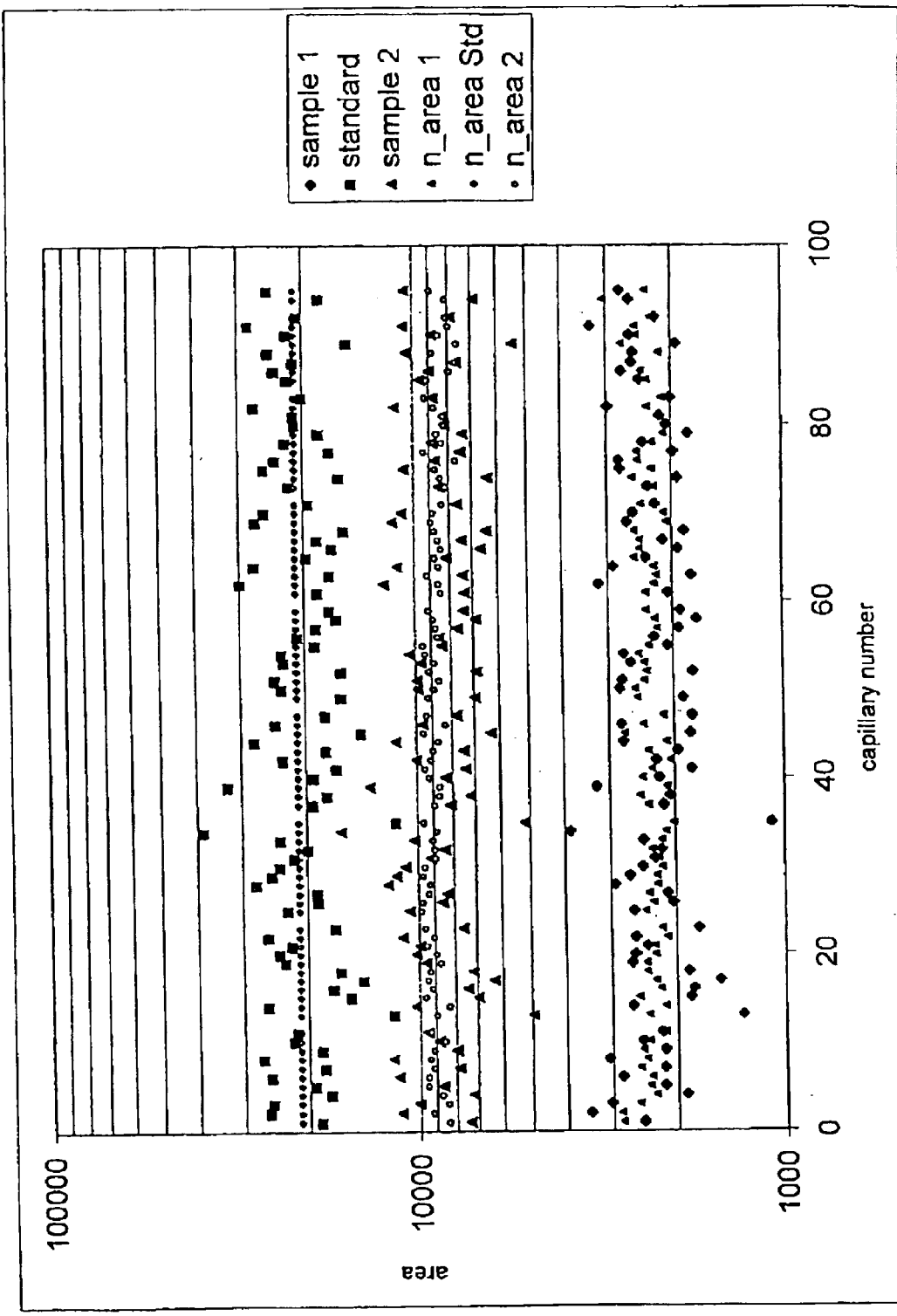
FIG. 14b illustrates the increased peak intensity precision achieved according to the present invention.

The improvement in the precision gained by normalizing the peak area and retention time to the internal standard as shown in Table 1 is further illustrated in FIGS. 14a and 14b. Ninety-six samples, each comprising two sample components and one reference sample component, were separated in a 96 capillary array. FIG. 14a shows a plot of the migration time of each of the two samples and the reference vs the capillary number. The data labeled sample 1, sample 2, and standard are the raw data from each capillary. In the absence of capillary to capillary variations, the data would be identical. The raw data, however, exhibit variations, which, if uncorrected, would introduce errors into a two-dimensional separation analysis. The data labeled n_time 1, n_time S, and n_time 2 correspond to the normalized retention time of the first sample, standard, and second sample, respectively. The normalized data clearly show the enhanced precision gained by normalizing.

FIG. 14b shows a plot of the peak area of each of the two samples and the reference vs the capillary number. The data labeled sample 1, sample 2, and standard are the raw data from each capillary. The data labeled n_time 1, n_time Std, and n_time 2 show the peak area, which has been normalized to the reference peak area as described above. The normalized data clearly show the enhanced precision gained by normalizing the peak area.

Figure 15:
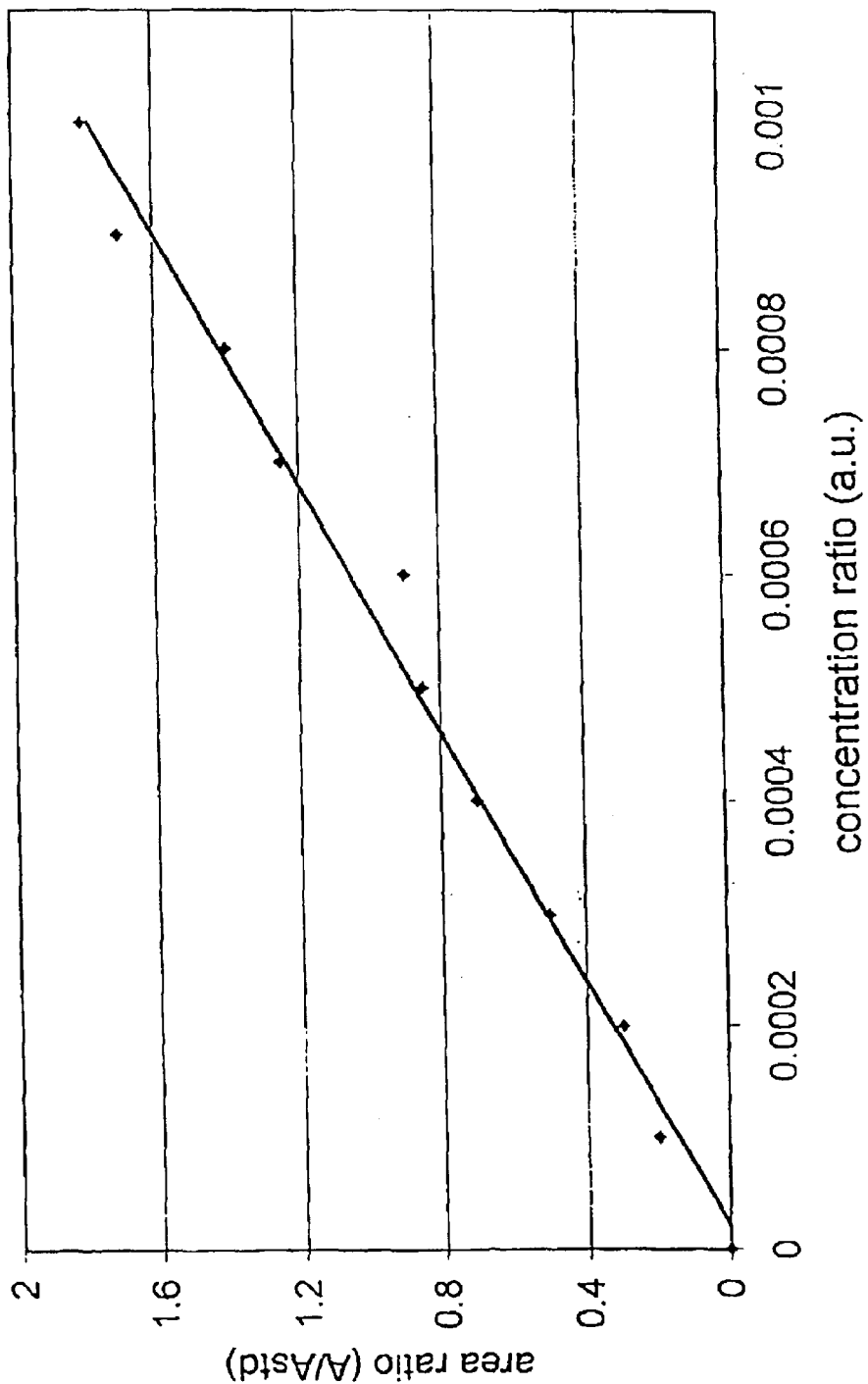
FIG. 15 presents a linearity plot.

FIG. 15 shows a plot of the ratio of the peak area of a first dye fluorescein to the peak area of a second dye, red food dye 41, as a function of the concentration ratio of the two dyes. The linearity of the plot shows the reference sample normalization technique can be used to normalize data over a wide range of sample concentrations even when there is a great disparity between the concentrations of the sample components. The area ratio is the measured peak area ratio of fluorescein to the red dye.

While the above invention has been described with reference to certain preferred embodiments, it should be kept in mind that the scope of the present invention is not limited to these. One skilled in the art may find variations of these preferred embodiments which, nevertheless, fall within the spirit of the present invention, whose scope is defined by the claims set forth below.

What is claimed is:

1. A method for separating components of a sample, comprising:
   obtaining a first separation of the sample components, wherein the first separation can be performed in the absence of an applied electric field;
   using an electric field to obtain a second separation of the sample components within a plurality of substantially isolated channels;
   obtaining an intensity-time data record from each of the isolated channels, each of the intensity-time data records comprising a first peak and a second peak; and
   normalizing a migration time of at least one of the first peaks with respect to an average migration time of a plurality of the second peaks to correct for migration time differences between the isolated channels.

2. The method of claim 1, wherein the second peaks correspond to the presence of a reference sample component added to the other sample components before the second separation of the sample components.

3. The method of claim 2, wherein the second peaks have a different fluorescence spectrum from other sample components and the different fluorescence spectrum is detected using a two-dimensional detector.

4. The method of claim 1, wherein normalizing a migration time comprises determining a ratio of the migration time of the first peak and the average migration time of the second peaks.

5. A method for separating components of a sample, comprising:
   obtaining a first separation of the sample components, wherein the first separation can be performed in the absence of an applied electric field;
   using an electric field to obtain a second separation of the sample components within a plurality of substantially isolated channels;
   obtaining an intensity-time data record from each of the isolated channels, each of the intensity-time data records comprising a first peak and a second peak; and
   normalizing an intensity of at least one of the first peaks with respect to an average intensity of a plurality of the second peaks to correct for intensity differences between the isolated channels.

6. The method of claim 5, wherein the second peaks correspond to the presence of a reference sample component added to the other sample components before the second separation of the sample components.

7. The method of claim 6, wherein the second peaks have a different fluorescence spectrum from other sample components and the different fluorescence spectrum is detected using a two-dimensional detector.

8. The method of claim 5, wherein normalizing an intensity comprises determining a ratio of the intensity of the first peak and the average intensities of the second peaks.

9. The method of claim 5, wherein the peak intensity is a peak area.

10. A system for separating components of a sample, comprising:
   a first separation device for obtaining a first separation of the sample components, wherein the first separation can be performed in the absence of an applied electric field;
   a second separation device for electrophoretically separating the sample components separated by the first separation device, the second separation device comprising a plurality of substantially isolated separation channels;
   a detection system to detect sample components within the substantially isolated separation channels and output detector signals indicative of the presence of the detected sample components; and
   a processor configured to receive the detector signals, determine a respective migration time of the detected sample components and normalize a migration time of a first sample component within at least one of the separation channels with respect to an average migration time of each of a plurality of respective reference sample components, the respective reference sample components having been separated along different ones of the substantially isolated separation channels to adjust for migration time differences between the isolated channels.

11. The system of claim 10, wherein the presence of the second sample components are indicated by peaks, each peak having a fluorescence spectrum different from other sample components and the detector comprises a two dimensional detector configured to detect the different fluorescence spectra.

12. The system of claim 10, further comprising an autosampler to collect fractions of eluant from the first separation device.

13. The system of claim 12, wherein the processor is further configured to increase a rate of fraction collection at a predetermined time.

14. The system of claim 13, wherein the time for increasing the rate of fraction follows detection of a peak having a peak width that exceeds a threshold.

15. The system of claim 10, wherein the isolated separation channels comprises a substrate defining a plurality of channels therein.

16. A system for separating components of a sample, comprising:
    a first separation device for obtaining a first separation of the sample components, wherein the first separation can be performed in the absence of an applied electric field;
    an electrophoresis device for obtaining a second separation of the sample components within a plurality of substantially isolated channels;
    a detector configured to obtaining an intensity-time data record from each of the isolated channels, each of the intensity-time data records containing a first peak and a second peak; and
    a processor configured to normalize an intensity of at least one of the first peaks with respect to an average intensity of a plurality of the second peaks to correct for intensity differences between the isolated channels.

17. A method for separating components of a sample, comprising:
    obtaining a first separation of the sample components, wherein the sample components are at least partially resolved on the basis of an isoelectric point of each component;
    using an electric field to obtain a second separation of the sample components within a plurality of substantially isolated channels;
    obtaining an intensity-time data record from each of the isolated channels, each of the intensity-time data records comprising a first peak and a second peak; and
    normalizing a migration time of at least one of the first peaks with respect to an average migration time of a plurality of the second peaks to correct for migration time differences between the isolated channels.

18. A method for separating components of a sample, comprising:
    obtaining a first separation of the sample components into a first plurality of sample volumes in the absence of an applied electric field;
    obtaining an electrophoretic separation of sample components present in each of the first plurality of sample volumes, wherein sample components present in different sample volumes are separated simultaneously along a respective one of a plurality of substantially isolated separation channels;
    obtaining an intensity-time data record from each of the isolated channels, each of the intensity-time data records comprising a first peak and a second peak; and
    normalizing a migration time of at least one of the first peaks with respect to an average migration time of a plurality of the second peaks to correct for migration time differences between the isolated channels.

19. A method for separating components of a sample, comprising:
    obtaining a first separation of the sample components into a first plurality of sample volumes in the absence of an applied electric field, at least some of the first plurality of sample volumes comprising at least partially separated sample components;
    obtaining an electrophoretic separation of the at least partially separated sample components of the first plurality of sample volumes to thereby form a plurality of substantially isolated volumes from each of said first plurality of sample volumes, the electrophoretic separation of respective first sample volumes being simultaneous;
    normalizing a migration time of at least one of the substantially isolated volumes with respect to an average migration time of a plurality of other of the substantially isolated volumes to correct for migration time differences between the isolated volumes.

20. The method of claim 19, wherein the migration time of the other of the substantially isolated volumes correspond to a migration time of peaks indicative of the presence of a reference sample component added to the first plurality of sample volumes.

21. The method of claim 20, wherein the reference sample component has a different fluorescence spectrum from other sample components and the different fluorescence spectrum is detected using a two-dimensional detector.

22. The method of claim 21, wherein normalizing a migration time comprises determining a ratio of the migration time of the first substantially isolated volume and the average migration time of the peaks of the reference sample component.

23. The method of claim 19, wherein a plurality of reference samples are added to each of the first plurality of sample volumes and normalizing a migration time comprises fitting a migration time of each reference sample to a polynomial function.

24. A method for separating components of a sample, comprising:
    obtaining a first separation of the sample components into a first plurality of sample volumes in the absence of an applied electric field, at least some of the first plurality of sample volumes comprising at least partially separated sample components;
    obtaining an electrophoretic separation of the first plurality of sample volumes to thereby form a plurality of substantially isolated volumes from each of said plurality of sample volumes, the electrophoretic separation of respective first sample volumes being simultaneous; and
    normalizing an intensity of at least one of the substantially isolated volumes with respect to an average intensity of other of the substantially isolated volumes to correct for intensity differences between the isolated volumes.

25. A system for separating components of a sample, comprising:
    a first separation device for obtaining a first separation of the sample components into a first plurality of sample volumes, wherein the first separation can be performed in the absence of an applied electric field, at least some of the first plurality of sample volumes comprising at least partially separated sample components;

a second separation device for electrophoretically separating each of the sample components, the second separation component comprising a plurality of substantially isolated separation channels;

an autosampler to collect the first plurality of sample volumes from the first separation device; and a processor configured to normalize a migration time of a first sample component within at least one of the separation channels with respect to a migration time of at least one reference component, to adjust for migration time differences between the isolated channels.

26. A separation method, comprising:

chromatographically separating a sample into a plurality of fractions, wherein the step of chromatographically separating can be performed in the absence of an electric field applied to the sample;

electrophoretically separating each fraction along a respective capillary, and presence of a reference standard;

obtaining an intensity-time data record from each of the capillaries, each of the intensity-time data records comprising a first peak and a reference standard peak, the reference standard peak indicative of the presence of the reference standard of the separation land in the capillary; and correcting a migration time of the first peak of the intensity-time data record from at least a first one of the capillaries for migration time variations between the capillaries based upon a migration time of the reference standard peak of the intensity-time data record from at least one of the other capillaries.

27. The separations method of claim 26, wherein correcting comprises normalizing the migration time of the first peak of the intensity-time data record from at least the first one of the capillaries with respect to the migration time of the reference standard peak of the intensity-time data record from the at least one of the other capillaries.

28. The separations method of claim 26, comprising automatically collecting each fraction from the chromatographic separation.

29. The separations method of claim 26, comprising combining each fraction with an identical reference standard.

* * * * *